United States Patent [19]
Schwartz

[11] Patent Number: 5,837,547
[45] Date of Patent: Nov. 17, 1998

[54] FLOW CYTOMETER CALIBRATION METHOD

[75] Inventor: Abraham Schwartz, Hato Rey, Puerto Rico

[73] Assignee: Caribbean Microparticles Corporation, Hato Rey, Puerto Rico

[21] Appl. No.: 579,186

[22] Filed: Dec. 27, 1995

[51] Int. Cl.⁶ ............................................... G01N 33/547
[52] U.S. Cl. .............................. 436/10; 436/8; 436/800; 435/967; 356/42; 356/243
[58] Field of Search .................... 436/8, 10, 15, 436/19, 800; 435/967; 356/42, 243

[56] References Cited

U.S. PATENT DOCUMENTS

| | | | |
|---|---|---|---|
| 3,836,849 | 9/1974 | Coulter et al. | 324/71 CP |
| 4,035,316 | 7/1977 | Yen et al. | 260/2.5 |
| 4,157,323 | 6/1979 | Yen et al. | 260/29.7 |
| 4,162,282 | 7/1979 | Fulwyler et al. | 264/9 |
| 4,170,685 | 10/1979 | Rembaum et al. | 428/402 |
| 4,247,434 | 1/1981 | Vanderhoff et al. | 260/29.6 |
| 4,254,096 | 3/1981 | Monthony et al. | 424/8 |
| 4,438,239 | 3/1984 | Rembaum et al. | 525/54.1 |
| 4,499,052 | 2/1985 | Fulwyler | 422/52 |
| 4,605,630 | 8/1986 | Kung et al. | 436/511 |
| 4,609,689 | 9/1986 | Schwartz et al. | 523/202 |
| 4,656,144 | 4/1987 | Hosaka et al. | 436/534 |
| 4,661,913 | 4/1987 | Wu et al. | 364/500 |
| 4,665,020 | 5/1987 | Saunders | 435/7 |
| 4,698,262 | 10/1987 | Schwartz et al. | 428/402 |
| 4,699,826 | 10/1987 | Schwartz et al. | 428/402 |
| 4,699,828 | 10/1987 | Schwartz et al. | 428/402 |
| 4,714,682 | 12/1987 | Schwartz | 436/10 |
| 4,727,020 | 2/1988 | Recktenwald | 435/6 |
| 4,751,188 | 6/1988 | Valet | 436/63 |
| 4,767,206 | 8/1988 | Schwartz | 356/73 |
| 4,774,189 | 9/1988 | Schwartz | 436/10 |
| 4,778,593 | 10/1988 | Yamashita et al. | 209/3.1 |
| 4,828,984 | 5/1989 | Schwartz | 435/7 |
| 4,857,451 | 8/1989 | Schwartz | 435/7 |
| 4,867,908 | 9/1989 | Recktenwald et al. | 252/408.1 |
| 4,868,126 | 9/1989 | Schwartz | 436/10 |
| 4,918,004 | 4/1990 | Schwartz | 435/7 |
| 4,987,086 | 1/1991 | Brosnan et al. | 436/501 |
| 5,073,497 | 12/1991 | Schwartz | 436/8 |
| 5,073,498 | 12/1991 | Schwartz et al. | 436/8 |
| 5,084,394 | 1/1992 | Vogt et al. | 436/8 |
| 5,089,416 | 2/1992 | Schwartz et al. | 436/8 |
| 5,093,234 | 3/1992 | Schwartz | 435/7.21 |
| 5,199,576 | 4/1993 | Corio et al. | 209/564 |
| 5,204,884 | 4/1993 | Leary et al. | 377/10 |
| 5,314,824 | 5/1994 | Schwartz | 436/10 |
| 5,380,663 | 1/1995 | Schwartz et al. | 436/10 |

OTHER PUBLICATIONS

Vogt, Jr. et al., "Model System Evaluating Fluorescein–Labeled Microbeads as Internal Standards to Calibrate Fluorescence Intensity on Flow Cytometerss" Cytometry 10:294–302 (1989).

Brown et al., "Controls for Flow Cytometers in Hematology and Cellular Immunology" Ann. New York Acad. Sci. 468, pp. 93–103 (1968).

*Primary Examiner*—Harold Y. Pyon
*Attorney, Agent, or Firm*—Olive & Olive, P.A.

[57] ABSTRACT

A method for calibrating a flow cytometer or fluorescence microscope and for quantitating binding proteins, such as antibodies. Populations of microbeads are provided which are in equilibrium with a saturating amount of fluorescently-labeled protein. The microbeads may have an incorporated fluorescent dye which has a strong signal in a selected channel of a flow cytometer, but no signal in other channels.

7 Claims, 3 Drawing Sheets

FLOW CYTOMETER CALIBRATION METHOD

BACKGROUND OF THE INVENTION

1. Field of the Invention

This invention relates generally to a method and kit for calibration of a flow cytometer or fluorescence microscope, and for performing quality control and quantitating binding proteins on samples.

2. Description of the Related Art

Fluorescence cytometry with flow cytometers or fluorescence microscopes is useful for studying particular cells which have been labeled due to the binding of specific labeled antibodies or other labeled proteins such as interleukins, antigens, cytokines, hormones, enzymes and filamental proteins.

Monoclonal antibodies are used as analytical probes for the detection of cell surface antigen expression, for example, on lymphocytes, granulocytes, platelets, erythrocytes, eosinophils, basophils, and stem cells to aid in clinical diagnosis and medical treatment of a variety of immunological diseases. Changes in the levels and ratios of different types of cells are often associated with particular diseases. Fluorescent labeling of antibodies which bind to these types of cells, or of other proteins which bind to the cells, together with flow cytometry, allows detection of cell populations which occur in small numbers and quantitation of fluorescence intensity and epitope expression.

Highly uniform microbeads having the same excitation and emission spectral properties as the samples under study have been used to calibrate flow cytometers. Plotting the calibration values of the microbeads against the relative fluorescence intensity peak channel for each microbead allows determination of the molecules of equivalent soluble fluorescent dye per sample particle (MESF) (U.S. Pat. No. 4,767,206). The disclosure of this patent and of all other patents and publications referred to herein is incorporated herein by reference. See also U.S. Pat. Nos. 4,774,189; 4,828,984; 4,868,126.

Fluorescent intensity microbead standards together with a single antibody binding population can be used to determine the "effective F/P ratio" which is the ratio of fluorescent dye molecules to the number of antibody molecules. Knowledge of the effective F/P ratio allows calculation of the average number of antibodies binding to cells which is determined by dividing the total number of fluorescent dye molecules associated with a particular antibody-labeled cell, determined via instrument calibration with appropriate microbead standards, by the F/P ratio.

Antibody binding calibration microbead standards, termed SIMPLY CELLULAR® microbeads, have been developed which directly bind antibodies and are used to construct calibration curves and determine the antibody binding capacity of labeled samples (U.S. Pat. No. 4,918, 004).

With the types of kits and microbeads known in the art, it often is inconvenient when the standards need to be labeled in a separate step, and/or the calibration line has to be plotted on graph paper. A further problem is that quality control is poorly defined in many systems due to a lack of a standardized mathematical definition of the calibration line and the performance parameters (e.g., sensitivity, linearity, dynamic range).

Use of computer programs allows calibration plots to be established and provides comprehensive quality control through linear regression and calculation of performance parameters for the instrument. Such parameters include average residual percent, coefficient of determination, detection threshold, coefficient of response, dynamic range, zero channel value of molecules of equivalent soluble fluorochromes (MESF) or antibody binding capacity (ABC) and maximum channel value of MESF or ABC. This allows the fluorescence intensity of samples to be relatively easily determined in MESF units (for microbeads) or ABC units (antibody binding capacity, for antibody-labeled samples; U.S. Pat. No. 5,380,663).

Although use of any single fluorescently-labeled antibody or other protein yields uniform and reproducible results with respect to performance parameters and binding quantitation, results are not as reproducible when proteins are obtained from different sources and/or conjugated to different fluorochromes. The variation may be explained in part by difference in isotypes, epitope specificity or clones. However, applicant has discovered that how the proteins are purified and conjugated to fluorochromes has major impact on their binding characteristics. As shown in Example III, Table 4 herein, conjugation of the same CD3 antibody to fluorescein isothiocyanate (FITC) and phycoerythrin (PE) yielded a 3-fold difference in binding capacity of human lymphocytes.

Furthermore, there is a variation in the results when there are different times of incubation of the microbeads together with the labeled cells, due to slower equilibrium binding kinetics with the microbeads. Reaching saturation with labeled microbeads and labeled cells is further complicated because of the different kinetics to reach saturation in each.

Therefore, as discussed in Example II (Table 2) herein, it has been found that using one set of calibrated binding capacities for microbeads has not been as accurate as expected for all different IgG antibodies (about 45% CV).

When certain lysing solutions for cells (for example, COULTER LYSE™, Coulter Corporation, Miami, Fla.) and instruments (for example, PROFILE II of Coulter Corporation) are used, light scatter signals of the standards overlap the light scatter of the cell samples. Therefore, the microbeads and cells cannot be gated separately and clear data for calibration curves cannot be obtained.

It is therefore an object of this invention to provide a method and kit to enable replication of results and correlation between different results when different antibodies, preparative methods, fluorochromes, stearic conditions, reagents and flow cytometers are used.

It is a further object of this invention to provide a method and kit to simplify and make more convenient the use of microbeads for instrument calibration and quantitation of protein binding.

Other objects and advantages will be more fully apparent from the following disclosure and appended claims.

SUMMARY OF THE INVENTION

Disclosed herein are a method and kit for calibrating a flow cytometer or fluorescence microscope and for quantitating binding antibodies, or other proteins, comprising providing populations of microbeads which are in equilibrium with a saturating amount of fluorescently-labeled protein, such as a fluorescently-labeled antibody. The microbeads preferably have an incorporated fluorescent dye which has a strong signal in a selected channel of a flow cytometer, but no signal in other channels. The kit includes a suspension containing protein-binding microbeads in equilibrium with the specific proteins which bind to the microbeads; and preferably, a software product containing a program for determination of selected performance parameters for quality control prior to determining the protein-binding capacity of samples. Additional information is preferably provided on the calibrated binding capacities of the various microbead populations.

Other aspects and features of the invention will be more fully apparent from the following disclosure and appended claims.

DETAILED DESCRIPTION OF THE INVENTION AND PREFERRED EMBODIMENTS THEREOF

Figure 1:
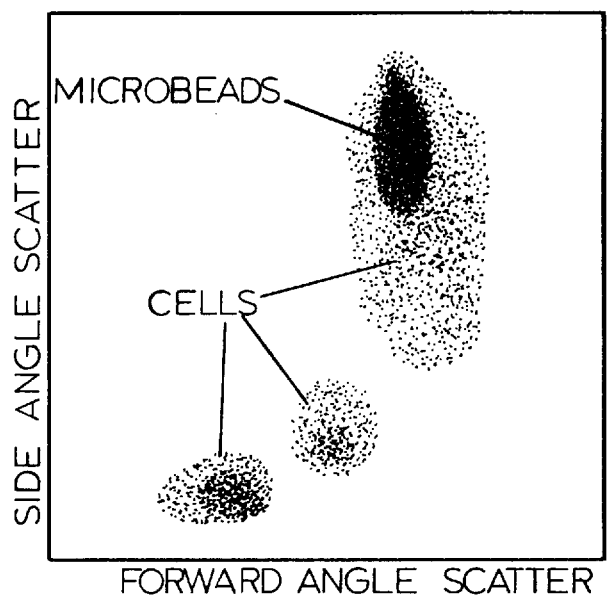
FIG. 1 is a bivariant forward v. side angle light scatter histogram of polymeric microbeads mixed with human leucocytes indicating that there is overlap of the microbead and cell signals (described in Example IV). Of the cell signals, the smaller lower left signals are the lymphocytes, the small central signals are the monocytes, and the larger signals overlapping the microbead signal are the granulocytes.

The present invention provides a method for calibrating a flow cytometer for use with fluorescently-labeled proteins which include antibodies, interleukins, antigens, cytokines, hormones, enzymes, and filamental proteins. The invention comprises a plurality of microbead populations which have a component on their surface which will bind different specific amounts of the selected proteins (called specific populations), including a microbead population which has no specific binding capacity for the selected protein. This plurality of microbead populations is suspended in a solution of excess (e.g., about 3-fold) selected protein to maintain equilibrium binding. The microbead populations preferably contain a fluorochrome which is easily measured by one of the fluorescence detectors of the flow cytometer, but is undetectable by the other fluorescence detectors. For example, the microbeads contain a far red fluorescence detectable by the FL3 detector, but which has no fluorescence signal in the FL1 or FL2 detectors.

As used herein, having the populations of microbeads "in equilibrium" with the saturating amount of fluorescently-labeled protein means that these components have been together in the mixture thereof for at least about 24 hours and preferably for at least a week prior to being used. In equilibrium, while there generally is not 100% saturation of the binding sites, one expects practically to have over about 90% saturation, and most likely over 95% saturation, when the mixture is at equilibrium, as in the invention herein.

In a first embodiment, the suspension of microbeads is washed prior to obtaining the calibration plot.

In an alternate second embodiment, the microbeads are added, without prior washing, to sample cells such that the excess fluorescent protein labels the sample cells, forming a mixture containing fluorescently-labeled microbeads and fluorescently-labeled sample cells. In this case, the mixture is incubated, lysed, and washed using standard procedures (for example, resuspend in phosphate-buffered saline, spin down in a centrifuge at about 2000G, and repeat resuspension and centrifugation at least one more time). The washed mixture is analyzed by gating on the microbeads in the mixture to determine representative peak channels, and using the representative peak channels and previously provided binding capacities of the microbeads to obtain a calibration plot, and to obtain performance parameters. In this alternative method, the fluorescently-labeled sample cells can then be gated with the flow cytometer or fluorescence microscope (assuming that the cells and microbeads are separately identifiable with a flow cytometer or fluorescence microscope) to determine the protein-binding capacity of the sample cells.

As used herein, the term "gating" refers to the practice of taking a selected population, for example, based on light scatter, and doing analysis only on that population, so that the resulting analysis is for that specific population only and is not made inaccurate by analysis of a mixed population. Gating preferably includes obtaining a dot plot of forward angle vs. the selected fluorescence channel for the fluorescent dye that the beads are stained with, drawing a box around groups of dots on the dot plot of the selected resolved populations of microbeads or sample cells, and obtaining a fluorescent histogram of each group using standard flow cytometry techniques.

While not necessary, it is preferred, whether the first or second embodiment is used, to incorporate a first fluorescent dye into the microbeads prior to labeling the microbeads with the fluorescently-labeled protein. The first fluorescent dye has a strong signal in a selected channel of a flow cytometer, but no signal in other fluorescence channels where the fluorescently-labeled protein has a signal. A useful dye for this procedure is oxazine I (Polyscience, Inc., Warrenton, Pa.). In this case, the fluorescently-labeled protein is labeled with a second, different dye, for example, fluorescein isothiocyanate or phycoerythrin. This refinement of the method and kit of the invention allows resolution of the microbeads from the cells by gating, because the microbeads labeled with the first fluorescent dye can be pulled out and analyzed separately from the cells without contaminating one population with the other.

The method and kit of the invention may be used with any type of cell sample as is known in the art, for example, lymphocytes, granulocytes, platelets, erythrocytes, eosinophils, basophils, and stem cells.

Preferably the method and kit of the invention include a software product which operates on a computer and contains information on the fluorescence intensity of each population of microbeads, and operates with the computer to control calculation of calibration and fluorescence information tailored to the microbead populations, for determination of selected performance parameters for quality control.

The method and kit of the invention may be used for increasing accuracy, precision and reliability of studies of binding quantitation of protein-labeled samples using a flow cytometer or fluorescent microscope.

In the overall procedure of the invention, any type of microbeads which are uniform in size and capable of uniformly binding the antibodies or other proteins which are to be used, may be employed. Preferred microbeads include those disclosed, for example, in U.S. Pat. No. 4,767,206, but microbeads having substantially different compositions than these may also be used.

The features and advantages of the present invention will be more clearly understood by reference to the following examples, which are not to be construed as limiting the invention. The first five examples describe experiments illustrating problems with prior calibration and quantitation methodologies, and the remaining examples relate to aspects of the invention herein.

EXAMPLES

EXAMPLE I

Preparation of Protein Binding Microbeads

Any microbead having the characteristics of high uniformity of size and distribution of functional groups may be used in the method and kit of the invention. One method of microbead preparation is as follows: suspend a highly uniform population of microbeads (i.e., having a size of 7–10μ diameter and a coefficient of variation in diameter of about 2% or less within a population, which contain free carboxyl groups on their surface in 0.1M HEPES at pH 4.5, and activated with a water soluble carbodiimide (1 ethyl-3-(3-dimethylaminopropyl) carbodiimide). Wash twice with 0.1M HEPES at pH 4.5, then with 0.1M HEPES at pH 7.0. Take aliquots of the activated microbeads and add different amounts of binding protein (e.g., goat anti-mouse IgG antibody) and allow the protein to covalently bind to the activated microbeads for at least four hours before washing four times with phosphate-buffered saline, pH 7.2 (PBS) containing 0.2% bovine serum albumin. An aliquot of microbeads not activated and not exposed to the binding protein serves as the non-binding (negative control) population.

EXAMPLE II

Variation of Binding Capacities of Standards Due to Source and Fluorochrome-conjugate of Antibody Antibody-binding capacities of four different microbead populations made according to Example I and being Fc specific, are determined for three different sources of two CD antigens. The same four microbead populations (1–4) were used for each of the four types of labeled antibodies (CD4-FITC, CD4-PE, CD8-FITC, and CD8-PE). The different antibodies compared in each group are specific for the same type of cells (CD4 or CD8) and are bound to the same fluorochrome.

All antibodies are titered to saturation by running different levels of antibodies with a given aliquot of microbeads to see where saturation occurs, exposed to microbeads for the same duration (60 minutes), and washed with PBS three times. Binding capacities are determined by direct relative linear channel proportionality (where the scale is directly proportional to the fluorescence intensity) with pooled normal peripheral lymphocytes using each respective antibody against levels of 50,000 for the CD4 antigen and 180,000 for the CD8 antigen. These levels are specified in the literature (e.g., Poncelet, P. et al., *Methods of Immunol. Anal.*, eds. Y. Masseyeff et al., 1993, 3:388–417) as being the binding capacity of these lymphocytes. Results are shown in Table 1.

TABLE 1

Binding Capacities with Respect to Source and Fluorochrome-conjugate of Antibody

| Bead Number | | BDIS[1] | Coulter[2] | Sigma[3] |
|---|---|---|---|---|
| CD4-FITC | 1 | 4223 | 8073 | 9651 |
| | 2 | 11396 | 18469 | 27458 |
| | 3 | 40420 | 56339 | 90052 |
| | 4 | 106873 | 127725 | 243529 |
| CD4-PE | 1 | 4634 | 6000 | 11920 |
| | 2 | 12176 | 14883 | 20858 |
| | 3 | 39096 | 46224 | 86812 |
| | 4 | 88784 | 95780 | 190322 |
| CD8-FITC | 1 | 4073 | 5882 | 2459 |
| | 2 | 10240 | 12980 | 8837 |
| | 3 | 35953 | 39242 | 34793 |
| | 4 | 93155 | 88965 | 97990 |
| CD8-PE | 1 | 6150 | 6436 | 3094 |
| | 2 | 15023 | 15399 | 11025 |
| | 3 | 45669 | 46555 | 49161 |
| | 4 | 94678 | 99705 | 121677 |

[1]Becton Dickinson, Sunnydale, CA.
[2]Coulter Corporation, Hialeah, FL.
[3]Sigma Immunochemicals, St. Louis, MO.

These results show the large differences between antibody binding capacity which vary depending on the source of the antibody and the fluorochrome-conjugate.

The average binding capacities of the four antibodies are shown in Table 2 below along with their percent coefficient of determination. This type of determination is preferably used to determine the assigned ABC of particular microbead populations for use in the method and kit of the invention herein. These results show the wide difference in binding capacities for the same microbead populations.

TABLE 2

The Average Binding Capacity and % Coefficient of Variation (% CV)

| Bead | Average Binding Capacity | % CV |
|---|---|---|
| 1 | 6049 | 45 |
| 2 | 15728 | 43 |
| 3 | 50859 | 37 |
| 4 | 120765 | 40 |

EXAMPLE III

Variation of Calculated Antibody Binding as a Function of Conjugated Fluorochrome As shown by the data presented below, the same CD3 clone (pan-lymphocyte marker) of monoclonal antibody conjugated to FITC or PE (Sigma Immunochemicals) yielded very different binding capacities on both normal and HIV sero-positive human peripheral lymphocytes, as well as on CYTOTROL® control cells (normal lyophilized lymphocytes) from Coulter Corporation (Miami, Fla.). The number of blood samples is indicated by "n". The blood samples were obtained from 55 laboratories in 9 different countries. The three-fold variation between the FITC and PE conjugates could be due to differences in binding to the microbeads or cells or both. These results show the effect of fluorochrome on the antibody binding capacity. Similar results are found with other types of cells. Thus, it is important to know that even if the same clone of cells is used, the fluorochrome can affect binding on the cells, beads, or both.

TABLE 3

ABC of Lymphocytes as a Function of Conjugated Fluorochrome

| Blood | CD3-FITC(n) | CD3-PE(n) |
|---|---|---|
| Normal | 178,000 (448) | 53,000 (414) |
| HIV Positive | 144,000 (333) | 44,000 (331) |
| Cytotrol | 176,000 (26) | 52,000 (46) |

EXAMPLE IV

Demonstration of Light Scatter Interference Between Cells and Microbeads

With certain instruments, such as Epics Profile from Coulter Electronics, and CytoronAbsolute from Ortho Diagnostic Systems, polymer microbeads fall in the same position on the light scatter bi-variant forward angle vs. 90° scatter histogram as cells, such as granulocytes. An example is shown in FIG. 1. This interferes with gating either population because of the overlap in spectra between the populations.

EXAMPLE V

Variation of Binding Capacities of Standards Due to Concentration and Incubation Time with Antibody Microbeads prepared as in Example I are exposed at room temperature for different amounts of time to the same antibody at either 10 µl or 20 µl antibody per 100,000 microbeads. These concentrations are at or near saturation of the binding capacity of the microbeads. The antibody used in this example is anti-CD4 obtained from Becton Dickinson Immunocytometry Systems, conjugated with fluorochrome phycoerythrin. The flow cytometer used for this study is a FACScan (Becton Dickinson Immunocytometry Systems). Results are shown in Table 4. Similar results are obtained with other types of microbeads that are uniform in size and are capable of uniformly binding the selected antibody or protein. These results show that although the antibody is at saturating concentrations, saturation is not reached in the half hour or the first hour of incubation, and therefore binding capacities of the different treatments increase with time of incubation. It can be seen from the above results that the microbeads do not reach an equilibrium peak channel after an hour, even though this is twice the time required for cells to reach equilibrium. Therefore, a higher amount of time to equilibrate the mixture is necessary for the invention herein.

TABLE 4

Peak Channel as a Function of Exposure Time

| | | Peak Channel (1024 Scale) | |
|---|---|---|---|
| Antibody | Time (mins) | 10 µl | 20 µl |
| CD4-PE | 1 | 584 | 673 |
| (BDIS) | 10 | 715 | 743 |
| | 20 | 749 | 761 |
| | 30 | 759 | 770 |
| | 40 | 767 | 776 |
| | 60 | 775 | 782 |

EXAMPLE VI

Demonstration of Saturation Stability of Antibodies in Equilibrium with Binding Microbeads Table 5 shows the intensity channel stability (peak channels) on a 1024 scale from mouse IgG binding microbeads, using a different lot of the same four populations of microbeads discussed above, which have been left to form an equilibrium with CD4-FITC antibody (Sigma Immunochemicals) for the specified number of hours prior to washing two times and analyzing with a FACScan Flow Cytometer. By the 96 and 385 hour sampling, an equilibrium had been reached.

TABLE 5

Intensity Stability of Antibody Binding Microbeads

| Bead | 1 hour | 96 hours | 385 hours |
|---|---|---|---|
| 1 | 262 | 293 | 289 |
| 2 | 408 | 436 | 432 |
| 3 | 555 | 582 | 584 |
| 4 | 711 | 734 | 741 |

EXAMPLE VII

Use of Fluorescence as a Gating Parameter

Figure 2:
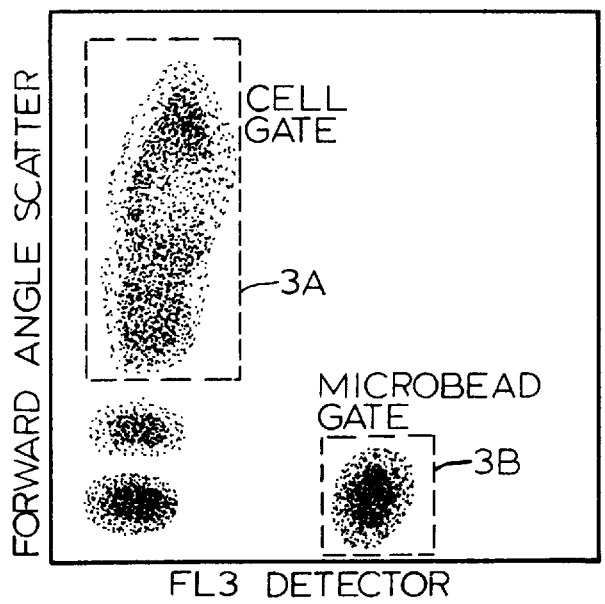
FIG. 2 is a bivariant forward angle light scatter vs. FL3 histogram of polymeric microbeads mixed with human leucocytes indicating that there is complete resolution between the microbeads and cell signals (described in Example VII). The gated cells are granulocytes, with the monocyte signals, and then the lymphocyte signals positioned below the granulocyte signal.
Figure 3A:
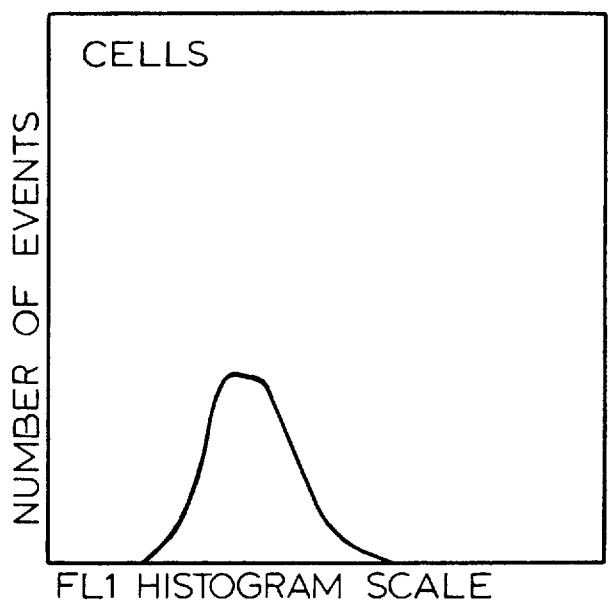
FIG. 3a is a FL1 histogram from gated microbeads (3a) in FIG. 2.
Figure 3B:
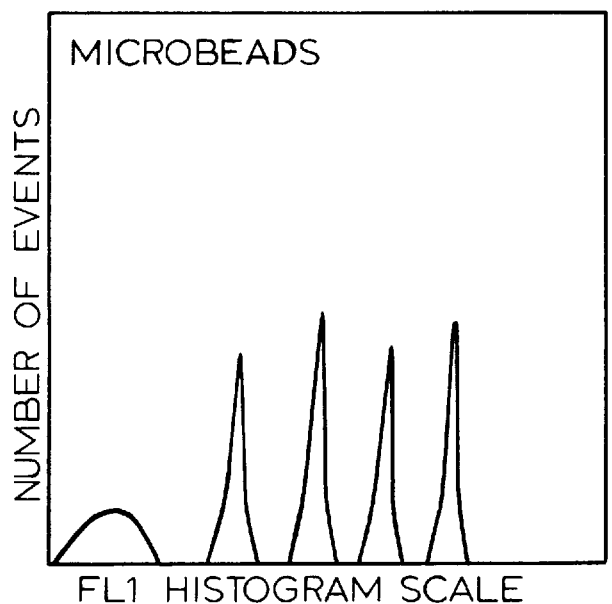
FIG. 3b is a FL1 histogram from gated cells (3b) in FIG. 2.

Microbeads dyed with Oxazine I in methanol to the intensity level where the FL3 channels show a signal brighter than the autofluorescence of the cells, but show no increase of intensity over unlabeled microbeads in the FL1 and FL2 channels, as shown in FIG. 2. Separate gating of the microbeads and cells is then accomplished using the FL3 vs. forward angle scatter bi-variant histogram as shown in FIGS. 3a and 3b. These results show that the use of an additional fluorescent dye allows separate gating of the microbeads and cells.

EXAMPLE VIII

Establishment of a Calibration Plot, Determination of Performance Parameters and Quantitation of Binding Capacity Using a Computer Program Pre-dyed (Oxazine I) goat anti-mouse binding microbeads in equilibrium with excess CD4-FITC antibody from Coulter Corporation are added to an equal volume (100 µl) human peripheral whole blood and allowed to incubate at room temperature for 30 minutes. The blood in the microbead mixture is then lysed with BDIS Lysing Solution for ten minutes and washed twice with PBS containing 0.5% paraformaldehyde. The sample is run on a FACScan flow cytometer (BDIS) and 20,000 events collected (an "event" is anything that triggers the instrument such as a microbead or cell). The listmode file is analyzed by first gating the microbeads in the forward vs. FL3 dot plot and determining their peak channels, then gating on the lymphocytes and determining their peak channels. These peak channels are then entered into the QUICKCAL® v. 2.0 program (Flow Cytometry Standards Corporation, San Juan, PR), and a calibration plot is established using linear regression.

Figure 4:
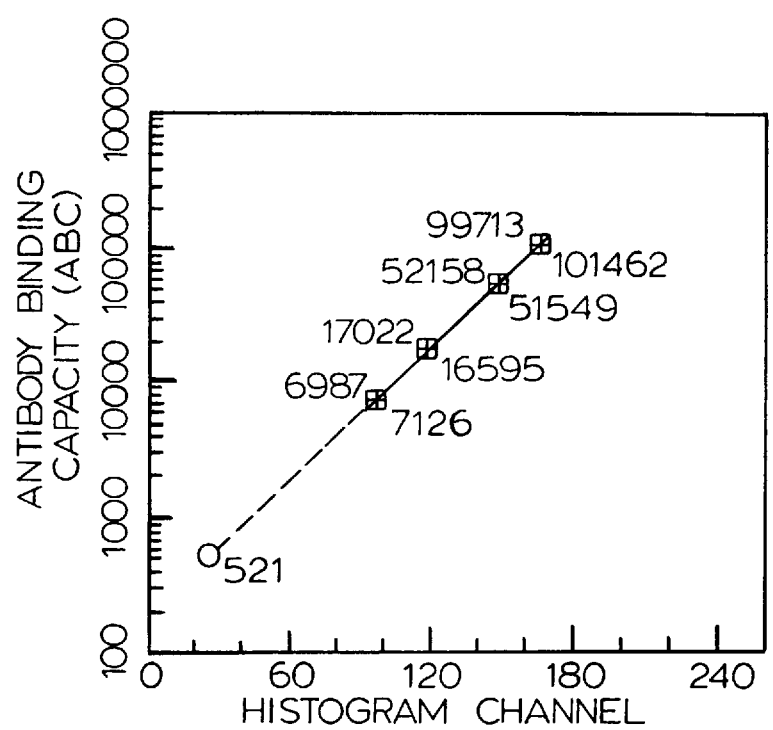
FIG. 4 is an example of a calibration plot according to the invention showing antibody binding capacity vs. histogram channel in Example VIII. The plot shows data points (+) for the microbead populations, best fit (□), and data point for the blank microbeads (o).

An example of such a calibration plot is shown in FIG. 4. The following acceptable performance parameters are associated with this particular example calibration plot: linearity (average residual percent)=1.86 (0–5); sensitivity (Detection Threshold)=521 (0–1000); and the dynamic range (Coefficient of Response=61.19 (59–69); ; Zero Channel Value in ABC units=196 (corresponds to left hand end of histogram); Maximum Channel Value in ABC units= 2885215) (corresponds to right hand end of histogram). The acceptable range for each parameter is shown in parentheses. These ranges are arbitrary values based on previous analyses of many instruments, which appear to be useful guidelines when comparing data from different instruments. Entering the peak channel for the lymphocytes yields a binding capacity of 64,682 ABC.

EXAMPLE IX

Indirect Staining of Binding Kit

Goat anti-mouse IgG binding microbeads in equilibrium with excess unlabeled CD8 antibody (Coulter Corporation) are added to human peripheral whole blood, incubated for 30 minutes and washed three times with PBS containing 0.2% bovine serum albumin (BSA). These are then labeled with a fluorescent ligand, such as goat anti-mouse conjugated to PE secondary antibody, and the blood lysed with BDIS Lysing Solution for ten minutes. After washing three times with PBS, the sample is run on a FACScan flow cytometer, and the listmode data analyzed by gating on the microbeads and cells respectively to determine their peak channels. These peak channels are analyzed with the QUICKCAL v. 2.0 program and yield the following performance parameters: AvRes%=2.8; Coeff. of Res.=63.2; Detection Threshold= 215 and Zero Channel Value=78. Entering the peak channel for the lymphocytes yields a binding capacity of 192,864. These results show that analogous to the previously discussed embodiments of the invention, microbeads in equilibrium with unlabeled antibodies or other proteins may be used for labeling with a secondary fluorescent antibody or other protein.

EXAMPLE X

Performing Calibration and Quantitative Binding Determinations While Performing Multiple-color Analysis Using the method of preparation of microbeads in Example I, two sets of calibrated binding microbeads (four populations per set) were prepared of different sizes, with the microbeads of a first set of microbeads having a diameter of $7\mu$ and the microbeads of the other set having a diameter of $10\mu$. The microbeads of these two sets had specific CD4 or CD8 antigens, respectively, conjugated to their surface. One drop of each of the microbead sets (microbead concentration of $2\times10^6$ per ml) were placed in a test tube and 100 $\mu l$ of whole blood was added. Fifteen microliters of anti-CD4-FITC and anti-CD8-PE (Becton Dickinson) were added to the mixture and allowed to reach equilibrium overnight according to the invention herein. The mixture was then lysed with FACS Lyse (Becton Dickinson) and washed twice with PBS and analyzed on a FACScan (Becton Dickinson). Gating on the $7\mu$ microbeads gave rise to the four populations labeled with CD4-FITC, and gating on the $10\mu$ microbeads gave rise to the four microbead populations labeled with CD8-PE. Gating on the lymphocytes gave rise to the separate cell populations labeled with CD4-FITC and CD8-PE. These data were entered into the QUICKCAL v. 2.0 program to determine the calibration plots which yielded binding capacities for CD4-FITC of 54,000 ABC and CD8-PE of 138,000 ABC.

EXAMPLE XI

Calibration of the Binding Capacity of Microbeads

One ml of a CD4-FITC mouse monoclonal antibody (Sigma Biosciences, St. Louis, Mo.) at a concentration of 50 ng/ml, plus one ml PBS, was analyzed in a Shimatzu Spectrofluorometer and found to have a fluorescence reading of 15.74. One ml containing $5\times10^6$ microbeads ($8.1\mu$) with goat anti-mouse antibody covalently bound to their surfaces, in PBS, was added to one ml of the antibody solution. The mixture was rotated overnight to reach equilibrium, and the microbeads were separated from the solution by centrifugation. The supernate was analyzed in the fluorometer and found to have a reading of 5.44. The background reading of PBS alone was subtracted from both the initial and equilibrium readings. This reading was subtracted from the stock solution reading to yield 10.30, representing the amount of antibody bound by the microbeads. By direct ratio, it was determined that this represents $1.34\times10^{11}$ molecules/ml of antibody removed from solution. Dividing this by the number of microbeads per ml yielded the antibody binding capacity of 53,800 antibodies/microbead.

The binding capacity of other proteins can be determined by the same method, and measurable labels other than fluorescent labels may be used, such as radiotracers, so long as they can be correlated with the concentration of the protein.

While the invention has been described with reference to specific embodiments thereof, it will be appreciated that numerous variations, modifications, and embodiments are possible, and accordingly, all such variations, modifications, and embodiments are to be regarded as being within the spirit and scope of the invention.

What is claimed is:

1. A method for increasing accuracy, precision and reliability of studies of protein-labeled cell samples using a flow cytometer or fluorescent microscope, comprising:
    (a) providing a microbead suspension containing:
        (i) a plurality of specific populations of microbeads which bind and are in equilibrium with a saturating amount of a selected protein; and
        (ii) a microbead population having no binding capacity for said selected protein;
    (b) providing information on calibrated binding capacities of the microbead populations;
    (c) using the microbead suspension to obtain a calibration plot by a method selected from the group consisting of:
        (i) washing the microbead suspension, analyzing the washed suspension on the flow cytometer or fluorescence microscope to determine representative peak channels, and using the representative peak channels and the calibrated binding capacities to obtain a calibration plot for the flow cytometer or fluorescence microscope, to obtain performance parameters and determine protein binding of cells; and
        (ii) adding the microbead suspension without washing, to sample cells, which fluorescently labels the sample cells due to the excess labeled protein, to form a mixture of microbeads and sample cells, incubating the mixture, washing the mixture, analyzing the washed mixture by gating on the microbeads in the mixture using the flow cytometer or fluorescence microscope to determine representative peak channels, and using the representative peak channels and the calibrated binding capacities to obtain a calibration plot for the flow cytometer or fluorescence microscope, to obtain performance parameters for using the flow cytometer or fluorescence microscope; wherein gating on the fluorescently-labeled sample cells with the flow cytometer or fluorescence microscope allows determination of the antibody-binding capacity of the sample cells.

2. The method of claim 1, wherein the protein is fluorescently labeled and is selected from the group consisting of fluorescently-labeled antibodies, interleukins, antigens, cytokines, hormones, enzymes, and filamental proteins.

3. The method of claim 1, wherein the protein is non-labeled and is selected from the group consisting of antibodies, interleukins, antigens, cytokines, hormones, enzymes, and filamental proteins, wherein the method further comprises washing the suspension and adding a labeled fluorescently-labeled ligand which binds to the non-labeled protein to label the microbeads to which the non-labeled protein is bound, after washing the microbead suspension.

4. The method of claim 1, further comprising incorporating a first fluorescent dye into the microbeads prior to labeling the microbeads with the fluorescently-labeled protein, which first fluorescent dye has a strong signal in a selected channel of a flow cytometer, but no signal in other channels where the fluorescently-labeled protein has a signal.

5. The method of claim 4, wherein the first fluorescent dye is oxazine I; and the fluorescently-labeled protein is labeled with a second, different dye selected from the group consisting of fluorescein isothiocyanate, phycoerythrin, and phycoerythrin-Texas Red.

6. The method of claim 1, wherein the sample cells are selected from the group consisting of lymphocytes, monocytes, granulocytes, platelets, erythrocytes, eosinophils, basophils, and stem cells.

7. The method of claim 1, further comprising providing a software product operating on a computer and containing information on a fluorescence intensity of each population of microbeads, the software operating with the computer to control calculation of calibration and fluorescence information tailored to the microbead populations, for determination of selected performance parameters for quality control, including linearity, sensitivity and dynamic range.

* * * * *